United States Patent
Tamarkin et al.

(10) Patent No.: US 7,340,297 B2
(45) Date of Patent: Mar. 4, 2008

(54) KIT, DEVICE AND METHOD FOR CONTROLLED DELIVERY OF OXIDIZING AGENT INTO THE SKIN

(75) Inventors: Dov Tamarkin, Maccabim (IL); Daniela Mavor, Tel Aviv (IL); Zvi Nitzan, Zofit (IL); Giora Arbel, Kfar Saba (IL); Nurit Harel, Tel Aviv (IL); Shalom Luski, Rehovot (IL); Yossi Gross, Moshav Mazor (IL)

(73) Assignee: Power Paper Ltd., Petah Tikva (IL)

( * ) Notice: Subject to any disclaimer, the term of this patent is extended or adjusted under 35 U.S.C. 154(b) by 99 days.

(21) Appl. No.: 10/858,045

(22) Filed: Jun. 2, 2004

(65) Prior Publication Data

US 2004/0267190 A1 Dec. 30, 2004

Related U.S. Application Data

(60) Provisional application No. 60/474,596, filed on Jun. 2, 2003.

(51) Int. Cl.
*A61N 1/30* (2006.01)
(52) U.S. Cl. ..................................... 604/20
(58) Field of Classification Search .............. 604/20; 424/78.07, 78.27, 62, 443, 449
See application file for complete search history.

(56) References Cited

U.S. PATENT DOCUMENTS

| | | | |
|---|---|---|---|
| 4,744,787 A | * | 5/1988 | Phipps et al. ............. 604/20 |
| 4,979,938 A | * | 12/1990 | Stephen et al. ............. 604/20 |
| 5,624,415 A | * | 4/1997 | Cormier et al. ............. 604/290 |
| 5,652,043 A | * | 7/1997 | Nitzan .................... 428/209 |
| 5,668,170 A | * | 9/1997 | Gyory .................... 514/449 |
| 5,792,097 A | * | 8/1998 | Reddy ..................... 604/20 |
| 5,911,223 A | * | 6/1999 | Weaver et al. ............. 128/898 |
| 6,078,842 A | * | 6/2000 | Gross et al. .............. 607/152 |
| 6,330,471 B1 | * | 12/2001 | Higo et al. ................ 604/20 |
| 6,667,052 B2 | | 12/2003 | Sintov et al. |
| 6,801,804 B2 | * | 10/2004 | Miller et al. .............. 604/20 |
| 6,970,739 B1 | * | 11/2005 | Inoue ..................... 604/20 |
| 2004/0167461 A1 | * | 8/2004 | Nitzan et al. .............. 604/20 |

FOREIGN PATENT DOCUMENTS

| EP | 0 318 776 | 6/1989 |
|---|---|---|
| EP | 0 900 576 | 3/1999 |

* cited by examiner

*Primary Examiner*—Kevin C. Sirmons
*Assistant Examiner*—Catherine N. Witczak
(74) *Attorney, Agent, or Firm*—Kenyon & Kenyon LLP

(57) ABSTRACT

A kit, device and method for delivering an oxidizing agent onto and/or into the body are disclosed. Moreover, a dermal patch device, which delivers an oxidizing agent using iontophoresis and or electroosmosis onto and/or into the body is disclosed. Furthermore, use of a dermal patch device for treatment of a body area with an oxidizing agent is disclosed. The device may be a thin and flexible dermal patch. A method of using such a device/kit for treatment of a disorder of a body area with an oxidizing agent is also disclosed.

37 Claims, 1 Drawing Sheet

KIT, DEVICE AND METHOD FOR CONTROLLED DELIVERY OF OXIDIZING AGENT INTO THE SKIN

CROSS REFERENCE TO RELATED APPLICATION

This application claims priority to U.S. Provisional Application No. 60/474,596, filed Jun. 2, 2003, the content of which is incorporated herein by reference in its entirety.

FIELD OF THE INVENTION

The present invention relates to kits, devices and methods for controlled delivery of agents onto and into a subject's body surface.

BACKGROUND OF THE INVENTION

Iontophoresis is an effective and painless method of delivering cosmetic and pharmaceutical agents to a localized tissue area by applying electrical current to a formulation of a medication comprising the agent or a precursor thereof. The two principal mechanisms by which electrical currents enhance molecular transport across the skin are: (a) Iontophoresis, in which a charged ion is repelled from an electrode of the same charge, and (b) Electroosmosis, the convective movement of solvent that occurs through a charged "pore" in response to the preferential passage of counter-ions when the electric field is applied.

Devices that deliver substances using iontophoresis have been developed for many applications, most of which involve the delivery of pharmaceutical compounds through the subject's skin and into the circulatory system or other organs of a subject's body. Topical application of one or more ingredient to the skin through the use of an iontophoresis device is called dermal treatment.

Oxidizing agents have many properties including therapeutic activity, such as antibacterial activity. Several oxidizing agents, which have anti-acne properties, are well known in the art. These include, for example, benzoyl peroxide, alpha hydroxy acids and detergents. Benzoyl peroxide is a strong oxidizing agent which may be used as an antibacterial and keratolytic agent in the treatment of acne. Other oxidizing agents, such as $NaClO_2$, which is sold under the trade name Dioxychlor, are useful in treating skin infections.

There is a recognized need for, and it would be highly advantageous to have, an improved method of administration of an oxidizing agent such as an iontophoresis/electroosmosis delivery system for delivering an oxidizing agent onto and into the body and a method of use thereof. It is desirable to have the benefit of treatment with an oxidizing agent, which is delivered with an iontophoretic device for increased penetration of the active oxidizing agent. Finally, it is desirable to have such a system, which has low cost. Preferably, such a system should be disposable.

SUMMARY OF THE INVENTION

Embodiments of the present invention include kits, devices and methods for delivery of an oxidizing agent onto and into a subject's body surface. Embodiments of the kits of the present invention may comprise an electrically powered patch and a formulation including an oxidizing agent or an oxidizing agent precursor. Embodiments of the devices of the present invention may comprise first and second electrodes, a power source and an oxidizing agent or an oxidizing agent precursor. Embodiments of the methods of the present invention may also comprise providing a device for treatment of a disorder comprising a flexible, wearable patch conformable to the contour of a body area surface, contacting the body area with the device for a time period wherein the device promotes oxidizing agent penetration of the body area surface and underlying tissues, penetrating of the oxidizing agent into and/or onto the body area to treat the body area disorder, and removing the device from the body area.

BRIEF DESCRIPTION OF THE DRAWINGS

With reference now to the drawings in detail, it is stressed that the particulars shown, are by way of example and for the purposes of illustrative discussion of embodiments of the present invention only, and are presented for providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms of the invention may be embodied in practice.

In the drawings.

DETAILED DESCRIPTION OF THE PREFERRED EMBODIMENTS

Figure 1:
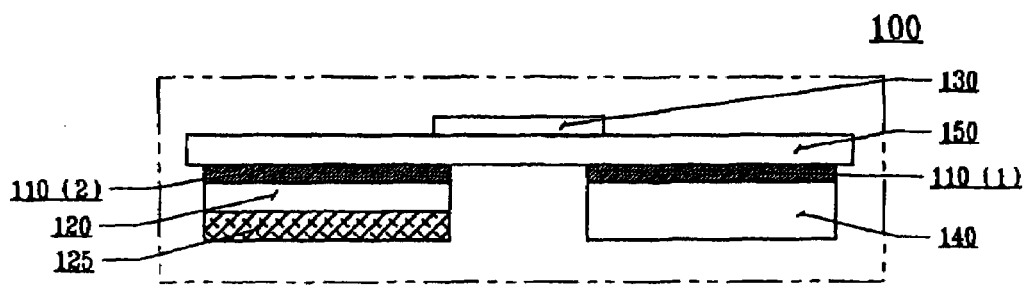
FIG. 1 shows a schematic view of one embodiment of a dermal patch for delivering an oxidizing agent of the present invention.
Figure 2:
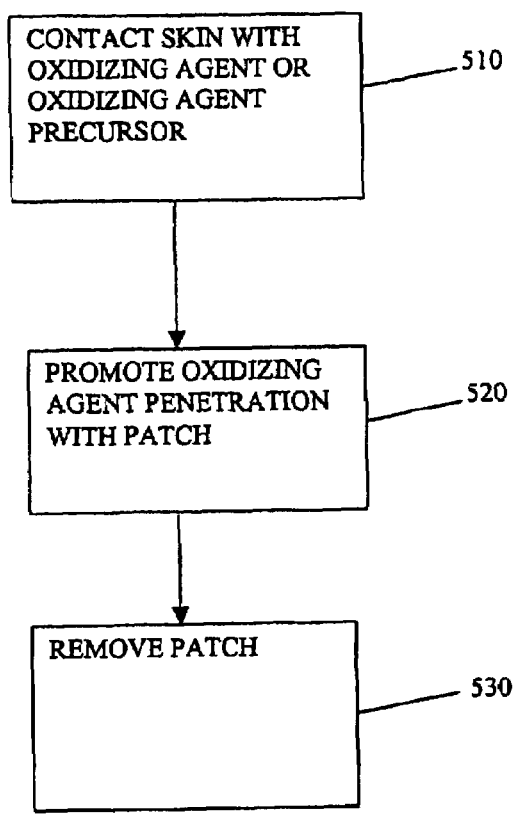
FIG. 2 is a flowchart of a method according to one embodiment of the present invention.

Disclosed herein is a kit, device and method for delivering an oxidizing agent onto and/or into the body. The kit and device may deliver an oxidizing agent using iontophoresis and/or electrosomosis onto and/or into the body. The kit and device may deliver an oxidizing agent using iontophoresis and/or electrosomosis for treatment of a body area with an oxidizing agent. Disclosed herein are examples of a device for a combination of surface treatment, dermal treatment and transdermal treatment of a body area. Preferably, the device is a thin and flexible dermal patch. Preferably, the body area is skin. Methods of use of such a device or kit for treatment of a body area with an oxidizing agent in accordance with embodiments of the invention are also presented herein.

Before explaining at least one embodiment of the invention in detail, it is to be understood that the invention is not limited in this application to the details of construction and the arrangement of the components set forth in the following description or illustrated in the drawings. The invention is applicable to other embodiments of being practiced or carried out in various ways. Also, it is to be understood that the phraseology and terminology employed herein is for the purpose of description and should not be regarded as limiting.

The principles and operation of kits and devices according to the present invention may be better understood with reference to the figures. The figures show embodiments of the present invention and are not limiting.

FIG. 1 shows a schematic view of a fully integrated patch device for delivery of an oxidizing agent according to one embodiment of the present invention. The patch device is fully integrated in the sense that an oxidizing agent or an oxidizing agent precursor is incorporated into the device. In this embodiment, patch 100 may comprise first electrode 110(1), identified as "cathode," second electrode 110(2), identified as "anode," and electrochemical cell 130 as the power supply of patch 100. Optionally, patch 100 may include a plurality of cathodes 110(1), a plurality of anodes 110(2) and a plurality of power supplies 130. Patch 100 may also comprise conductive layer/s 120 and 140 to provide an interfacing layer between patch 100 and a body area of a subject. One of or both conductive layer/s 120 and 140 optionally include oxidizing agent or oxidizing agent precursor 125. As shown in FIG. 1, electrodes 110(1) 110(2), conductive layers 120, 140, oxidizing agent 125, and electrochemical cell may be supported on substrate 150. Electrode 110(1) may be disposed in any suitable way on substrate 150 in spaced relation to electrochemical cell 130 and electrode 110(2) to define a gap between the two electrodes. Conductive layer 120 including oxidizing agent or oxidizing agent precursor 125 may optionally be disposed on electrode 110(2) or 110(1) or on both electrodes 110(1) and 110(2). In an alternative embodiment, patch 100 does not include conductive layer 120 (or conductive layer 140). In this alternative embodiment oxidizing agent or oxidizing agent precursor 125 can optionally be accommodated in a holding component, such as a chamber (not shown in figure), which may be attached to electrode 110(1) or electrode 110(2). Alternatively, oxidizing agent or oxidizing agent precursor can be accommodated on electrode 110(1) or 110(2) in any other suitable way.

As noted, the embodiment depicted in FIG. 1 is a fully integrated patch device. The present invention may also be practiced with a patch device that does not have an oxidizing agent or an oxidizing agent precursor incorporated into it, but which instead is part of a kit. Such a patch device is similar to the embodiment of the fully integrated patch device depicted in FIG. 1. However, in this alternative embodiment, the conductive layer 120 of the patch optionally (when it is part of a kit) does not include an oxidizing agent or oxidizing agent precursor 125. Alternatively, oxidizing agent or oxidizing agent precursor 125 accommodated in conductive layer 120 may be disposed in a separate holding component (not shown), which may not be integrally attached to the patch. Optionally, separate holding component can be attached to patch just before use, such as for example when separate holding component is a chamber. Alternatively, separate holding component can be applied onto body area, such as for example when separate holding component is a sponge or other type of material absorbing device. Alternatively, oxidizing agent or oxidizing agent precursor 125 accommodated in conductive layer 120 may be applied directly onto body area or onto electrode, without use of a separate holding component.

Optionally, oxidizing agent or oxidizing agent precursor 125 can be disposed on anode or on cathode or on both anode 110(2) and cathode 110(1). In one non-limiting example when two reactants/precursors react with each other when there is a passage of current, resulting in production of an oxidizing agent, one reactant/precursor can be disposed on the anode 110(2) and the other reactant/precursor can be disposed on the cathode 110(1). Preferably, oxidizing agent or oxidizing agent precursor 125 is disposed on anode 110(2).

Certain features of the patch of the present invention 100 that are the same regardless of whether the patch 100 is a fully integrated patch device or a patch that is part of a kit will now be described. Preferably, patch 100, including patch components, is thin and flexible, to suit the contour of a body area of a subject. Preferably, patch 100 is electrically powered. Patch may be any size, color and shape suitable for application to a desired body area. The thickness of patch 100 is preferably up to 10 mm to ensure flexibility, but may be thicker, depending on the application. The thickness of the patch may also be dependent upon the type of material used and the flexibility of that material. Patch 100 is preferably disposable, but may be reusable. Patch 100 is stable to a wide range of temperatures and humidity.

Any power supply 130, of any size or shape, which provides an electrical potential of between about 0.2 Volt and about 100 Volt can be used according to the present invention. Yet, in a preferred embodiment, power supply 130 is an electrical battery, providing an electrical potential of between about 1.5 Volt and 12 Volt.

Preferably, power supply 130 is thin and flexible. Preferably, power supply thickness should not exceed 4 mm and more preferably, power supply thickness should be less than 2 mm. In a further preferred embodiment, power supply 130 is at least one electrochemical cell. The term 'electrochemical cell' as used herein includes any suitable cell in which chemical energy is converted to electric energy by a spontaneous electron transfer reaction. The term includes cells with non-spontaneous reactions, cells with spontaneous reactions, galvanic cells, electrolytic cells and a combination thereof. Preferably, electrochemical cell includes a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and (c) a water soluble polymer for obtaining a required viscosity for adhering the first and second layers to the third layer. Such a power source is described in U.S. Pat. Nos. 5,652,043, 5,811,204 and 5,897,522, which are incorporated herein by reference in their entireties. However, the use of any power source consistent with a flexible wearable device is within the scope of the invention.

Optionally, power supply 130 in patch 100 is a single electrochemical cell. However, power supply 100 need not be limited to one cell, but may include a plurality of connected electrochemical cells, a plurality of batteries, and/or electronics configured to increase, control, and change phase of the supplied electric current and wherein the power supply is thin and flexible. Electrochemical cell 130 in patch 100 preferably provides electrical potential (voltage) to the desired body area of the subject. In a preferred embodiment, the electrical potential may be adjusted to satisfy at least one of the following three criteria.

First, the patch voltage may be adjusted to enable an iontophoretic delivery of the oxidizing agent/s into the body area. Second, the patch voltage may be adjusted to minimize the penetration of the oxidizing agent/s through the body, and to maximize the amount into the desired body area. Third, the patch voltage may be adjusted to minimize body area irritation, which may result from excessive electric current, passing into and through the body.

The power supply may optionally be located in any suitable position on the patch.

A power supply to the patch may provide a duty cycle and pulse partition rate of between about 1% and about 99%. The frequency of the power supply may preferably be from about 1 Hz to about 1000 Hz. The power supply may provide voltage in a range of from about 0.2V to about 100V to the patch.

Cathode and anode electrodes 110(1) and 110(2) are preferably composed of a conductive material. Preferably, at least one electrode is an active electrode and at least one electrode is a counter electrode. Optionally, the active electrode can be the cathode or anode or both the cathode and the anode. Defining which electrode is the active electrode is dependent on the charge of the formulation or oxidizing agent being used. Any suitable conductive material may optionally be used, such as, but not limited to silver, silver/silver chloride, graphite, zinc, copper, carbon, platinum, manganese dioxide or a combination thereof. In a preferred embodiment, at least one of the electrodes may include zinc, copper, silver and silver/silver chloride. Any other suitable conductive element or compound, including metal and non-metal materials, can be used as electrode materials. The electrodes may optionally be provided in any suitable form, such as, but not limited to as thin sheets, linked to the power source, or printed onto a substrate in spaced relation to each other to define a gap therebetween. Optionally, the electrode area can be continuous, or formed in any shape or configuration. Optionally, cathode 110(1) and anode 110(2) may not have the same shape and/or same area. Optionally, cathode and anode may be in any suitable conformation in relation to each other including but not limited to a coplanar and cofacial arrangement. Optionally, patch can include a plurality of anodes and a plurality of cathodes. Such a multi-electrode patch facilitates providing simultaneously a plurality of treatments with one oxidizing agent or a plurality of oxidizing agents in different body areas or the same body area.

Preferably, cathode 110(1) and anode 110(2) are connected to battery 130 by any suitable connection means 155, such as electrical conduction means/media 155. Examples of connection means 155 include, but are not limited to wiring, conductive ink, printed connection means, soldered connection means, connection means attached by UV, glued connection means and a combination thereof.

Substrate base layer 150 is optionally any suitable material, which can accommodate the oxidizing agent delivery patch components. Suitable materials include, but are not limited to woven material, non-woven material, polymers, conducting material, non-conducting material, paper, cardboard, plastic, synthetic materials, natural materials, fabric, metals, wood, glass, Perspex, or a combination thereof. Preferably, substrate material is a non-conductive material. More preferably, substrate is made from polyester. Optionally, substrate base layer 150 can be made up of a plurality of substrate base layers 150, which can be stacked or connected in a co-planar way by any suitable attachment means. Preferably, substrate layer 150 is made up of one continuous piece of substrate layer 150. Optionally, substrate base layer 150 can be any suitable size, shape or color.

Optionally, substrate base layer 150 may readily facilitate attachment of the device 100 to a desired body area. Attachment mechanisms may include but are not limited to conductive adhesive, adhesive strip, suction cups and/or any combinations thereof. In the embodiment of FIG. 1, patch 100 is configured to attach to the body area by conductive layer 140. In alternate embodiments, the patch may be attached to the body area by, for example, the frame of the substrate and/or other attachment mechanisms.

Conductive layers 120 and 140 may optionally be any suitable conductive composition, such as an aqueous gel, hydrogel or a conductive adhesive.

In the embodiment shown in FIG. 1, anode electrode 110(2) is active. However, either anode electrode 110(2), cathode electrode 110(1), or both electrodes may be active for delivering an oxidizing agent. Thus, at least the features of the patch of the present invention described above are the same regardless of whether the patch is a fully integrated patch device, or a patch included as part of a kit.

Optionally, oxidizing agents according to the present invention may be part of a formulation, placed in the interface area between one or both of the electrodes of the device. Providing that they possess a certain degree of water solubility, they can be mobilized from the formulation towards the body surface, via the electromotive forces of iontophoresis and/or electro-osmosis. The term 'formulation' as used herein includes any type of suitable formulation, which can accommodate an oxidizing agent or oxidizing agent precursor. The term includes conductive layers, such as aqueous gel or hydrogel. The term further includes any pharmaceutical or cosmetic active or inactive formulation, including active ingredients, solvents, fragrance and additives. Additives to such formulations include but are not limited to water, surfactants, emulsifiers, diglycerides, triglycerides, stabilizing agents, thickening agents, alpha-hydroxy carboxylic acids, antioxidants, preservatives, moisturizers, petroleum, mineral oil, glycerol, ethanol, propanol, isopropanol, butanol, polymeric gelling agents, flavoring, colorant and odorant agents and other formulation components, used in the art of pharmaceutical and cosmetic formulary. In an embodiment, wherein the oxidizing agent is placed in the interface area between one or both of the electrodes, the formulation containing the oxidizing agent can optionally be applied directly onto the skin between the two electrodes, or alternatively the oxidizing agent is disposed in a holding component, such as, but not limited to a sponge placed between the two electrodes or applied onto the substrate between the two electrodes. Preferably, the formulation is contained in a conductive layer, such as, but not limited to, a hydrogel.

Optionally, holding component may be any suitable means for accommodating oxidizing agent, such as, but not limited to a sponge, a chamber and substrate. Preferably, holding component may be made from a non-woven and non-conductive material.

Patch preferably results in current flow between electrodes through the conductive composition containing oxidizing agent. Preferably, flow of current facilitates production and flow of oxidizing ions from the components, such as oxidizing agent disposed in conductive composition/formulation. The produced ions provide surface treatment of skin.

Alternatively, oxidizing agents or oxidizing agent precursors may be embedded or disposed on the surface of one or both of the device electrodes (as shown in FIG. 1), which readily facilitates delivery of the oxidizing agent from the electrode area towards the body surface using iontophoresis and/or electroosmosis. Optionally, electrode can be manufactured with oxidizing agent or precursor mixed with electrode material.

Optionally, the formulation containing the oxidizing agents can be applied directly onto the skin or can be applied onto the electrode or to the interface area between one or both of the electrodes.

The term 'oxidizing agent' as referred to herein includes any suitable oxidizing agent including any substance, which will readily add or take on electrons. Oxidizing agent includes inorganic and organic oxidizing agents, such as, but not limited to quinones. Oxidizing agents according to the present invention also include agents, which can spontaneously exert an oxidizing effect on a body organ living cells and pathogens. In addition, oxidizing agents according to the present invention include, but are not limited to oxidizing agents or oxidation agents in any suitable form, such as a liquid, semi-liquid, semi-solid, solid, gaseous, semi-gaseous, pure oxidizing agent, oxidizing agent or oxidizing agent precursor as part of a formulation, mixtures of more than one oxidizing agent and any combination thereof. Examples of suitable oxidizing agents include, but are not limited to oxygen; peroxides, such as hydrogen peroxide and benzoyl peroxide; elemental halogen species, as well as oxygenated halogen species, such as hypochlorite ions and perchlorite species. In one embodiment, the oxidizing agent may be applied to the device of the present invention. In an alternative preferred embodiment, the oxidizing agents are produced in-situ from a precursor, upon closure of an electrical circuit. Still in another preferred embodiment, the oxidizing agent is produced by any suitable electrochemical reaction, such as a redox process, or electrolysis upon closure of an electrical circuit. Examples of such electrochemical and redox processes, yielding oxidizing agents are presented below in Table 1:

TABLE 1

| Precursor | Oxidizing agent | E° (V) |
| --- | --- | --- |
| $I^- + 2\ OH^-$ | $IO_3^- + 3\ H_2O$ | 0.26 |
| $OH^-$ | $O_2 + 2\ H_2O$ | 0.41 |
| $2\ OH^-$ | $IO^- + H_2O$ | 0.485 |
| $2\ I^-$ | $I_2$ | 0.535 |
| $H_2O_2$ | $O_2 + 2\ H^+$ | 0.695 |
| $Cl^- + 4\ OH^-$ | $ClO_2^- + H_2O$ | 0.76 |
| $Cl^- + 2\ OH^-$ | $ClO^- + H_2O$ | 0.841 |
| $Cl^-$ | $Cl_2$ | 1.358 |
| Hydroquinone 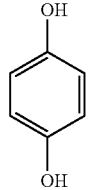 | Quinone 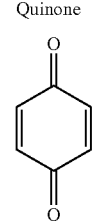 | 0.09 |

Thus, including at least one precursor in the electrode mass, or as an embedded layer on the surface of one or both of the electrodes, or in the formulation interfacing between the electrodes and a body surface or one precursor or reactant on one electrode and a second precursor or reactant on a second electrode and closing an electrical circuit, preferably in a potential higher than required to generate the respective oxidizing agent via a redox process, evolves an active oxidizing agent. The strength of the electrical current (i.e., current density) and the precursor concentration are preferably both positively correlated with the amount of oxidizing agent evolved.

As previously stated herein oxidizing agents according to the present invention include agents that may spontaneously exert an oxidizing effect on a body organ living cells and pathogens. Such effect may result in therapeutic affects as exemplified in the following list:

Pathogen Killing

Oxidizing agents are generally capable of killing pathogens. Bacterial pathogens are generally classified, in a non-limiting fashion, as follows:

Gram positive bacteria, such as the aerobic cocci *Staphylococcus aureus* and *Staphylococcus epidermidis*; aerobic rods, e.g., *Bacillus anthracis, Bacillus cereus, Lactobacillus* sp., *Listeria monocytogenes, Corynebacterium diptheriae* and *Propionibacterium acnes*; anaerobic rods, such as *Actinomyces* sp. *Clostridium botulinum, Clostridium difficile* and *Clostridium perfringens*; and Anaerobic, Gram-positive cocci.

Gram negative bacteria include, for example, Aerobic, Gram-negative cocci, e.g., *Neisseria gonorrhoeae, Neisseria meningitides* and *Moraxella catarrhalis*; anaerobic, Gram-negative cocci; aerobic, Gram-negative rods, including *Fastidious* Gram-negative rods, *Enterobacteriaceae* (glucose-fermenting Gram-negative rods), oxidase-positive glucose-fermenting Gram-negative rods glucose-nonfermenting Gram-negative rods; and anaerobic Gram-negative rods.

There are also Bacteria, which cannot or are difficult to Gram stain.

Infections caused by dermatophytes—fungi that invade only dead tissues of the skin or its appendages (stratum corneum, nails, hair). Trichophyton, Epidermophyton, and Microsporum are most commonly involved.

Yeast infections of skin (usually of moist, occluded, intertriginous areas), skin appendages, or mucous membranes caused by yeasts of the genus *Candida*.

Yet, another class of pathogens include Common, contagious types of human papillomavirus.

Thus, such pathogens are generally susceptible to oxidation, and treatment with an oxidizing agent readily facilitates curing and, alleviating the symptoms of or prevention of diseases and disorders, associated with the occurrence of the pathogens. Thus the kit and device of the present invention readily facilitates treatment of diseases and disorders, which are susceptible to oxidation with an oxidizing agent.

In addition, oxidizing agents are also commonly used for accomplishing bleaching or whitening effects. This may be useful, for example in the whitening or lightening of the skin and teeth. Therefore, the device or kit of the present invention can be used for skin and teeth whitening or lightening.

Once evolved, the oxidizing agent is preferably delivered towards a body surface by an electromotive process, known as "Iontophoresis". As described above iontophoresis can be defined as a mean of enhancing the flux of ionic compounds across a membrane, by the application of an electric current across it. This technique has been reported useful for the enhancement of transdermal delivery of ionized drugs, including macromolecules. The skin is a multilayered organ delimiting the body. It is constituted of several layers and the outermost layer, stratum corneum, is the main barrier to drug transport. The application of electric current, however, is able to increase the penetration of molecules through this barrier. The two principal mechanisms by which iontophoresis enhances molecular transport across the skin are:

(a) iontophoresis, in which a charged ion is repelled from an electrode of the same charge, and
(b) electroosmosis, the convective movement of solvent that occurs through a charged "pore" in response to the preferential passage of counter-ions when the electric field is applied. Electroosmosis is useful for the delivery of uncharged, yet, water soluble molecules.

As used herein the term 'iontophoresis' includes, but is not limited to iontophoresis, electroosmosis or iontophoresis in combination with another mechanism and a combination thereof.

The strength of the electrical current (i.e., voltage and current density), and the oxidizing agent concentration are both positively correlated with the amount of oxidizing agent evolved. Modulation of these two parameters is useful in adjusting the amount of the oxidizing agent, available in the target body surface and the underlying body layers.

Other parameters, which may influence the rate of oxidizing agent migration and tissue availability, are pH, electrode surface area, formulation properties, viscosity, adhesiveness and conductivity of the formulation interfacing between the electrodes and the body surface.

The therapeutic system of the present invention may further comprise any additional therapeutic agents or active agents or additives, which may contribute to the therapy of the disorder or another related or unrelated disorder.

Non-Limiting Examples of skin disorders which can benefit from the oxidizing agent treatment, are set forth in Table 2.

TABLE 2

A non-exhaustive listing of dermatological disorders, which can benefit from the oxidizing agent treatment.
Dermatological Disorder Bacterial Infections of the Skin Cellulitis
Acute Lymphangitis
Lymphadenitis
Erysipelas
Cutaneous Abscesses
Necrotizing Subcutaneous Infections
Staphylococcal Scalded Skin Syndrome
Folliculitis
Furuncles
Hidradenitis Suppurativa
Carbuncles
Paronychial Infections
Erythrasma
Fungal Skin Infection Infections caused by dermatophytes, fungi that invade only dead tissues of the skin or its appendages (stratum corneum, nails, hair)
Infections of skin (usually of moist, occluded, intertriginous areas), skin appendages, or
mucous membranes caused by yeasts of the genus Candida.
Viral Skin Infection Warts
Herpes
Disorders of the Hair Follicles And Sebaceous Glands Acne
Rosacea
Perioral Dermatitis
Scaling Papular Diseases Pityriasis Rosea
Pityriasis Rubra Pilaris
Pigmentation Disorders Hyperpigmentation
Malignant Tumors, which nay be responsive to oxidizing agent treatment Basal Cell Carcinoma
Squamous Cell Carcinoma
Malignant Melanoma
Kaposi's Sarcoma The body area to be treated with the device and oxidizing agent of the present invention includes, but is not limited to skin, keratinized tissue, nails, teeth, hair, organ, non-malignant growth and tumor. Preferably, the body area to be treated with the oxidizing agent is skin. Preferably, the device and kit of the present invention is for use on humans. Optionally, the device and kit of the present invention can be used on non-humans. The patch and kit of the present invention may be applied by the subject himself or by a third party. The patch and kit of the present invention readily facilitates home use in addition to use in a clinic or other supervised environment.

Preferably, treatment according to the present inventions may be beneficial in all body areas. Treatments of the oral cavity using oxidizing agents according to the present invention is also of high benefit. Non-limiting examples of oral disorders, suitable for treatment according to the present invention, include bacterial, fungal and viral infections of the oral cavity. Teeth whitening using oxidizing agents according to the present invention is also very useful. In addition, the patch and kit of the present invention including any suitable oxidizing agent or oxidizing agent precursor may optionally be used to reduce dental hypersensitivity, in oral anesthesia, plaque removal, ulcer treatment and for fluoride treatment. Likewise, treatment of any mucosal disorder which is responsive to treatment with oxidizing agents is included in the scope of the present invention.

In a preferred embodiment, wherein the patch is thin, flexible and versatile in shape and form, the preferred devices of the present invention can be designed to fit any area of the body surface and to have any desirable size, according to the area having the disorder.

The patch of the present invention may be made using any suitable techniques. Preferably, the patch of the present invention is a printed patch, wherein the electrodes and power supply are printed onto the substrate using any suitable printing technology.

FIG. 5 is a flowchart of a method according to embodiments of the present invention. The flowchart applies to a non-limiting method using a fully integrated patch, or to a method using a kit including a patch. First, a subject may contact (510) a body area with an oxidizing agent/or oxidizing agent precursor/s (which may or may not be an integrated part of a patch). The subject may promote (520) penetration and/or generation of oxidizing agent onto and/or into the body area through the use of an electrically powered patch. The patch is removed from the body area (530) at the end of the treatment time. Optionally end of treatment time is determined by depletion of the active agent and/or sufficient therapeutic effect of the treatment or by a predetermined time.

While the principles of the invention have been discussed in relation to exemplary embodiments discussed herein, it is understood that the principles of the invention are not limited thereto.

EXAMPLE NO. 1

Oxidizing Agents and Their Precursors

Examples of such electrochemical/redox processes, yielding oxidizing agents are presented in Table 1 above.

In one non-limiting example hydrogen peroxide is used as an oxidizing agent with the kit/device of the present invention to treat a skin infection. Hydrogen peroxide is placed in a formulation containing hydrogel on the anode. When the patch is contacted with the infected skin area of the subject, current flows and oxygen is produced in situ. The oxygen is delivered dermally to treat the infection.

EXAMPLE NO. 2

Treatment of Skin Infection With an Oxidizing Agent

Many people worldwide suffer from skin infections. Treatment of skin infections includes use of the oxidizing agent $NaClO_2$, which is sold under the trade name Dioxychlor.

Use of the kit or dermal patch of the present invention is effective in the treatment of skin infections. Preferably, the patch or kit is used with a formulation including the oxidizing agent $NaClO_2$ resulting in iontophoretic treatment and topical treatment of skin infections. Optionally, any suitable formulation including the oxidizing agent $NaClO_2$ is envisioned for use with the dermal patch. The oxidizing agent $NaClO_2$ is preferably contained in the hydrogel to form a mixture. The mixture can optionally be applied directly to the desired area of the body. Alternatively, the mixture is preapplied, such as, but not limited to, during manufacture of the patch, onto the electrode/s of the patch and therefore the patch is ready for use. Further, the aqueous hydrogel can be contained in a separator, which is integrally formed with the patch or in a holding component disposed between the two electrodes. Still further, the mixture can be contained in a separate, non-integral holding component, such as a retainer. The retainer is then optionally connected to the patch before use.

A typical method of treatment includes the following steps of adhering the patch of the present invention to the desired area of the body, such as, but not limited to the face and back. One area or more than one area of the body can be treated at the same time using a plurality of patches or the same patch with a plurality of electrodes. If the kit of the present invention, which includes a separate retainer is being used, the retainer which preferably contains $NaClO_2$ mixture is first attached to the patch before adhering to the skin. In the case where a patch of the present invention is being used, which does not include hydrogel, the aqueous hydrogel can be applied directly to the place of treatment on the body of the subject. In the case that the hydrogel is contained in the patch, the patch is ready to use.

Adhering the patch to the skin closes the electrical circuit. Current will then flow, resulting in iontophoresis and electrical stimulation of the skin and dermal and transdermal penetration of the $NaClO_2$ oxidizing agent ions. The duration of treatment is determined according to severity of condition and other skin factors. A typical treatment session lasts between about 10 to about 20 minutes. Treatment is terminated by removal of the patch. Alternatively, treatment is terminated by depletion of the battery, at least one of the electrodes or depletion of the oxidizing agent.

Typically, the treatment is repeated in selected time intervals. At the beginning, the treatment is usually repeated more frequently, such as a few times a week and then for maintenance of the resulting effect, the treatment is repeated less frequently.

Those skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A kit, comprising:
    a formulation comprising at least one oxidizing agent precursor; and
    an electrically powered patch to promote electrical conversion of the at least one oxidizing agent precursor into an active oxidizing agent and delivery of the active oxidizing agent onto and/or into a body area,
    wherein the patch is configured to provide an electrical potential sufficient to generate the active oxidizing agent determined according to the standard potential of the oxidizing agent and/or oxidizing agent precursor.

2. The kit of claim 1, wherein the patch is an iontophoretic patch.

3. The kit of claim 1, wherein the patch comprises:
    at least one active electrode;
    at least one counter electrode; and
    at least one power supply to supply electrical energy to the at least one active electrode and the at least one counter electrode, wherein the at least one power supply is supported on a base member.

4. The kit of claim 3, wherein the at least one power supply comprises at least one electrochemical cell.

5. The kit of claim 4, wherein the electrochemical cell is thin and flexible.

6. The kit of claim 4, wherein the electrochemical cell comprises:
    a first layer of insoluble negative pole;
    a second layer of insoluble positive pole; and
    a third layer of aqueous electrolyte disposed between the first and second layers and including:
        a deliquescent material to keep the electrochemical cell wet at all times;
        an electroactive soluble material to obtain ionic conductivity; and
        a water-soluble polymer to obtain a desired viscosity to adhere the first and second layers to the third layer.

7. The kit of claim 3, wherein the at least one oxidizing agent precursor is disposed in an interface area between the at least one active electrode and the at least one counter electrode.

8. The kit of claim 1, wherein the patch comprises at least one active electrode, and the at least one active electrode is at least one of an anode, a cathode or both an anode and a cathode and wherein the at least one oxidizing agent precursor is disposed on the at least one active electrode.

9. The kit of claim 1 further comprising a holding component that holds and stores the oxidizing agent formulation to contact a first region of the body area and the at least one active electrode.

10. The kit of claim 9, wherein the holding component is selected from the group consisting of a sponge, separator, non-woven material, or substrate base layer.

11. The kit of claim 1, wherein the at least one oxidizing agent precursor is applied directly to the body area.

12. The kit of claim 1, further comprising:
    a conductive layer comprising a conductive composition to provide a conductive layer between the patch and the body area.

13. The kit of claim 12, wherein the conductive composition is a hydro gel.

14. The kit of claim 12, wherein the at least one oxidizing agent precursor is contained in the conductive composition.

15. The kit of claim 12, wherein the conductive layer is disposed on the at least one active electrode.

16. The kit of claim 1, wherein the body area is selected from the group consisting of skin, teeth, nails, hair, non-malignant growth, tumor and a combination thereof.

17. The kit of claim 1 for treatment of a disorder, wherein the disorder is selected from the group consisting of a bacterial infection, a viral infection, a fungal infection, a mucosal disorder, scaling diseases, tumors, body area discoloration and a combination thereof.

18. The kit of claim 1, wherein the patch is thin and flexible.

19. The kit of claim 1, wherein the patch is a printed patch.

20. The kit of claim 1, further comprising an additional active medicinal ingredient.

21. The kit of claim 1, wherein the current density of the electrical potential and/or the concentration of the at least one oxidizing agent precursor is positively correlated with the amount of the active oxidizing agent.

22. The kit of claim 1 for treatment of a fungal infection of the nail.

23. A device comprising:
   at least one first electrode adapted to communicate an active substance into a body area by application of an electrical current on a body surface adjacent to the body area;
   at least one second electrode, facilitating closing of electrical circuit with the body surface;
   at least one power source to provide a current and voltage, connected through a conductive media to the first and second electrodes; and
   at least one oxidizing agent precursor,
wherein the device is configured to provide an electrical potential sufficient to generate an active oxidizing agent from the at least one oxidizing agent precursor determined according to the standard potential of the oxidizing agent and/or oxidizing agent precursor and deliver the active oxidizing agent onto and/or into a body area.

24. The device of claim 23, further comprising a holding component for holding the at least one oxidizing agent precursor.

25. The device of claim 24, further comprising a conductive layer comprising a conductive composition disposed between the patch and the body area, for providing a conductive interfacing layer between the patch and the body area, wherein the conductive layer is disposed on at least one of the group selected from the first electrode, the second electrode and the first and the second electrode, the holding component, the body area surface and a combination thereof.

26. The device of claim 25, wherein the conductive composition comprises the at least one oxidizing agent precursor.

27. The device of claim 23, wherein the at least one oxidizing agent precursor is mixed within the material of one or both of the at least one first and the at least one second electrodes.

28. The device of claim 23, wherein the at least one oxidizing agent precursor is disposed in an area between the first electrode and the second electrode.

29. The device of claim 23, wherein the electrical voltage and current facilitate conversion of the at least one oxidizing agent precursor into an oxidizing agent.

30. The device of claim 23, wherein the electrical voltage and current facilitate delivering the oxidizing agent, topically or via iontophoresis, to the body surface.

31. The device of claim 23, wherein the power supply comprises at least one thin and flexible electrochemical cell.

32. The device of claim 23, wherein the patch is thin and flexible.

33. The device of claim 23, wherein the electrodes and power source are applied using a printing technology onto the patch substrate.

34. The device of claim 23, further comprising a substrate base layer.

35. A method of treating a body area with an oxidizing agent comprising:
   converting electrically at least one oxidizing agent precursor into an oxidizing agent by providing an electrical potential sufficient to generate an active oxidizing agent determined according to the standard potential of the oxidizing agent and/or at least one oxidizing agent precursor; and
   delivering iontophoretically the resulting oxidizing agent, facilitating oxidizing agent penetration of the body area surface and underlying tissues and treatment of the body area.

36. A device comprising:
   at least one first electrode adapted to communicate an active substance into a body area by application of an electrical current on a body surface adjacent to the body area;
   at least one second electrode, facilitating closing of electrical circuit with the body surface;
   at least one power source to provide a current and voltage, connected through a conductive media to the first and second electrodes; and
   an oxidizing agent precursor for generating in situ an oxidizing agent for treatment of a body area
   wherein the generated oxidizing agent is the active substance.

37. The device of claim 36, wherein the oxidizing agent is electrochemically generated.

* * * * *